United States Patent [19]

Higo

[11] Patent Number: 4,785,677

[45] Date of Patent: Nov. 22, 1988

[54] PIPETTING DEVICE HAVING AN AUTOMATIC MECHANISM FOR REPLACING NOZZLE TIPS

[75] Inventor: Yuji Higo, Nagoya, Japan

[73] Assignee: Toyo Soda Manufacturing Co., Ltd., Shinnanyo, Japan

[21] Appl. No.: 52,053

[22] Filed: May 21, 1987

[30] Foreign Application Priority Data

May 21, 1986 [JP] Japan ................................ 61-117110
Jul. 7, 1986 [JP] Japan ................................ 61-159474

[51] Int. Cl.⁴ .............................................. B01L 3/02
[52] U.S. Cl. ............................. 73/864.14; 73/864.11; 422/100
[58] Field of Search .......... 73/863.32, 864.01, 864.14, 73/864.11; 422/100; 141/3, 21, 25, 84, 98; 222/192, 522, 525, 566, 575

[56] References Cited

U.S. PATENT DOCUMENTS 4,555,957 12/1985 Frankel et al. .................. 73/864.14

Primary Examiner—Mark J. Thronson
Attorney, Agent, or Firm—Oblon, Fisher, Spivak, McClelland & Maier

[57] ABSTRACT

A pipetting device is formed of a supporting frame, a slider mounted on the supporting frame for vertical movement, a plunger type stem having a lower end fittable within the upper end of an approximately inverted cone shaped nozzle tip, the stem being mounted for vertical movement on the slider, and a conduit for supplying the lower end of the stem with an air supply and exhaust device so that the nozzle tip may be communicated with air or air may be sucked therefrom. A rotating cam cooperates with a pin on the slider for vertically moving the slider by a large stroke. An air cylinder has a piston fixed relative to the stem for vertically moving the stem by a small stroke. A lever loosely mounted on the lower end of the stem can engage the nozzle tip for removing the nozzle tip from the stem.

9 Claims, 5 Drawing Sheets

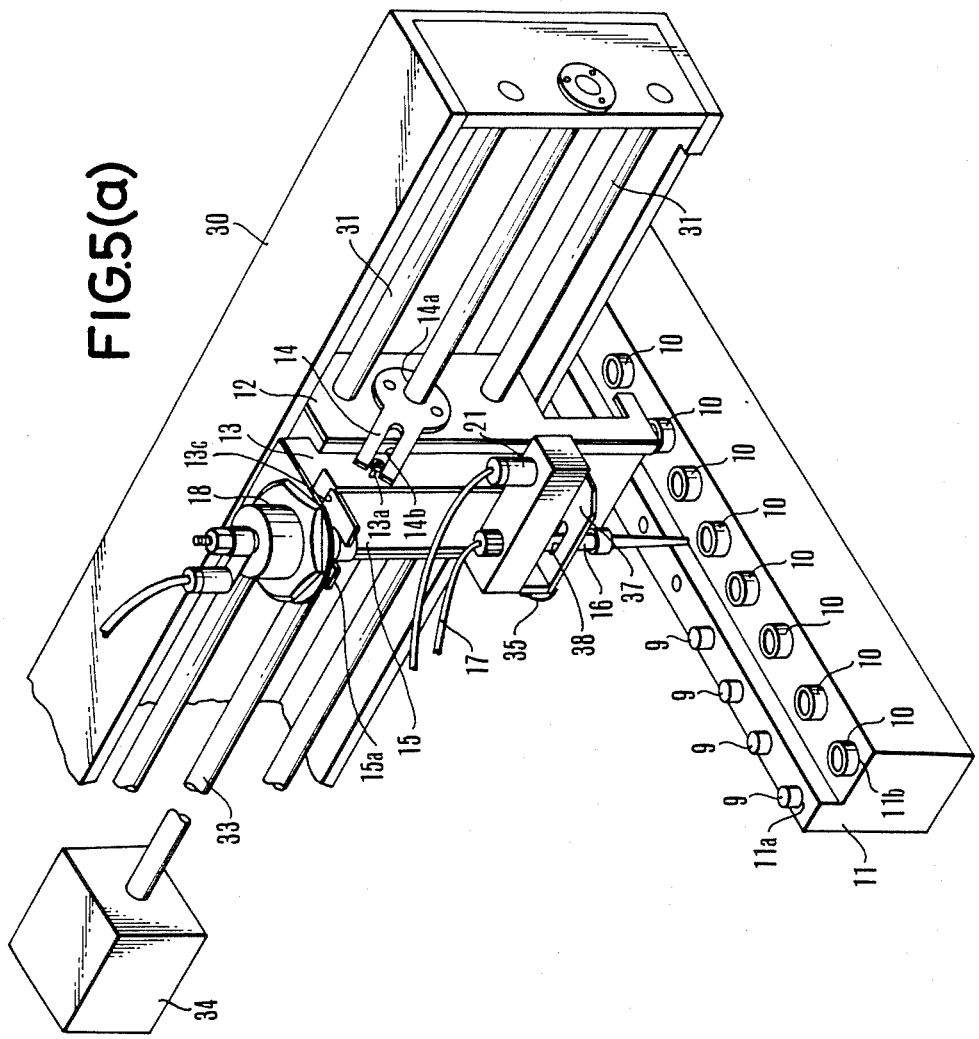

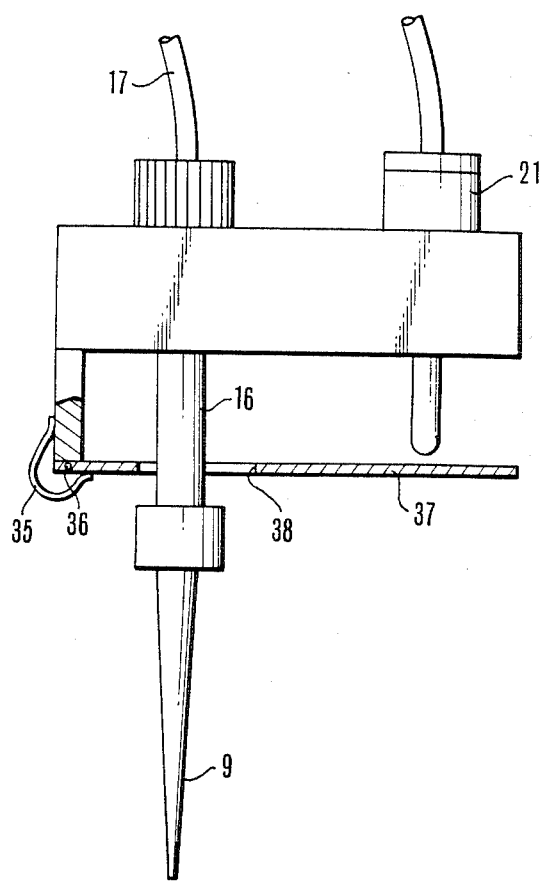
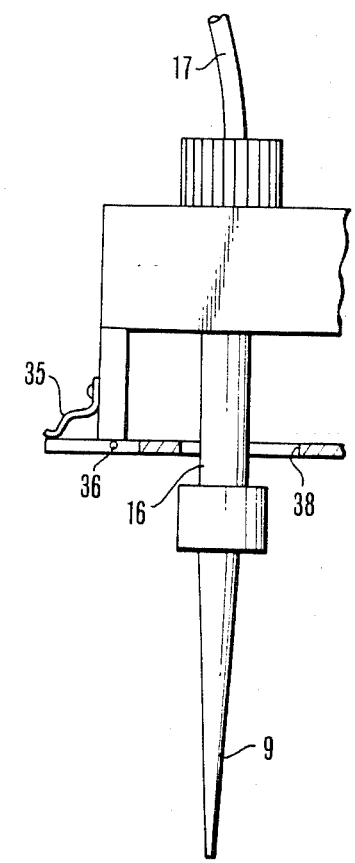

PIPETTING DEVICE HAVING AN AUTOMATIC MECHANISM FOR REPLACING NOZZLE TIPS

BACKGROUND OF THE INVENTION

1. Field of the Invention

The present invention relates to a pipetting device for automatic injection of minute volumes of a solution which is used in an apparatus for automatically and continuously measuring a number of (solution) samples, and more particularly, to a pipetting device having an automatic mechanism for providing a new nozzle tip for each sample by fitting a disposable nozzle tip (hereinafter designated simply as a nozzle tip) to the lower end of the nozzle of the pipette. Thus, the automatic mechanism of the pipetting device enables one to provide a new nozzle tip to every new sample.

2. Background of the Related Art

Generally, when a minute amount of a substance in a sample solution is to be detected either by an immunological reaction or any other chemical or biochemical means, an appropriate reagent is added to the sample solution, a change provoked in the solution is detected and the magnitude of the change is measured for this end, skill is often required for the quantitative operations of measuring the sample solution and injecting the reagent solution.

Speaking generally, however, these operations are mostly so tedious and tiresome that troubles arise in handling minute amounts of sample and reagent solutions with a high accuracy and precision over extended periods. It is also desired to reduce the differences in the magnitude of errors between individual operations as much as possible. Further, the number of skilled operators falls far below the increasing number of samples. For these reasons, various investigations and developments have been made for automated devices by which determination and detection of minute substances can be performed by use of biochemical techniques.

As an instrument for the estimation of minute constituents in sample solutions, any automated apparatus must be capable of treating minute quantities of substances. On the other hand, when samples of different natures are to be estimated successively, where the concentration ratio of a substance between samples is up to $1:10^6$ (in the case of $\alpha$-protein, for example), mixing of sample solutions in the apparatus should be minimized in order to attain high accuracy together with a low degree of error in the treatment.

SUMMARY OF THE INVENTION

In view of the above considerations, it is an object of the present invention to provide a pipetting device which is capable of injecting a plurality of sample solutions quantitatively into a plurality of reaction cells which are prepared and arrayed therebelow.

Another object of the invention is to provide a pipetting device having a mechanism by which a nozzle tip used for each of the sample solutions can be automatically replaced.

The present invention satisfies the above objects and includes a plunger-type stem having a lower end fitted in the upper end of a nozzle tip having approximately the shape of an inverted cone. The stem is connected to an air supply and exhaust device for both suction and delivery of a solution. A slider supports the stem so that the stem can be moved by a small stroke in the vertical direction. A supporting frame supports the slider so that the slider can be moved in the vertical direction by a large stroke. A power driving means moves the slider by the large stroke and another power driving means moves the stem by the small stroke in the vertical direction on the slider. A lever is installed around the lower end of the stem for removing a nozzle tip fitted to the stem by applying pressure on the upper end of the nozzle tip. A power means drives the lever for removing the nozzle tip.

In the present invention, the stem is moved in both large and small strokes in the vertical direction. This assures tight fitting of the nozzle tip to the stem without causing breakage of the tip, in view of tolerances in the manufacture of the nozzle tips.

The pipetting device of this invention may be used in two ways. In one, the device is fixed in a position and test plates which support reaction cells are successively moved in and out. In the other, the pipetting device scanningly moves over reaction cells arranged in rows.

In addition, the vertical movement by a large stroke of the stem may also be utilized in connection with the functions of the pipetting device, i.e., suction and delivery of solutions.

The driving means should achieve a precise position of the stem with a relatively small number of strokes and this is done by using an air cylinder device, a pulse motor, a screw driving device, a cam mechanism, etc. Particularly when breakage of a nozzle tip before it is fitted to the stem is feared, an air cylinder device is preferred as the second power driving means because the downward driving force of the stem is conveniently limited to a certain level or less. Another measure is a buffering mechanism in which an excessive force over a certain limit is absorbed with a bending spring board.

Nozzle tips which fit to the stem and are replaceable in their use may be conventional, but naturally they should be of a capacity large enough to accommodate a sample solution without contact between the solution and the lower end of the stem (usually a capacity of several $\mu l$ to ml will suffice).

The present invention can be preferably used as an analytical appliance mainly of biochemical reactions, particularly for an apparatus with which an immunological reaction is measured using an enzyme, for example, as a label. Of course, application is not limited to the examples, but naturally extends to a variety of analytical purposes in which a number of sample solutions are to be injected in continuous analytical measurements.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5(a) is an orthogonal view showing an example of a different embodiment of this invention; and FIG. 5(b) is an enlarged view showing the mechanism for removing the nozzle tip.

FIG. 5(c) shows a modification of the nozzle tip removing mechanism.

DETAILED DESCRIPTION OF THE PREFERRED EMBODIMENTS

The present invention will now be explained in reference to preferred embodiments of a device for enzymatic immunological measurement where a reaction cell which is packed inside with beads is used as a test cup, as shown in the Figures.

The reaction cell 8 is a cup-shaped vessel with an open upper end, containing a plurality of beads. The upper opening of the reaction cell is tightly closed with a sealing foil. The beads contain a particular antigen (or antibody) fixed beforehand to their surface, so as to provide a reaction cell suitable for the desired items of examination. The beads may contain a magnetic substance to achieve agitation of liquid in the reaction cell in synchronization with an alternating magnetic field applied from the outside.

Figure 1:
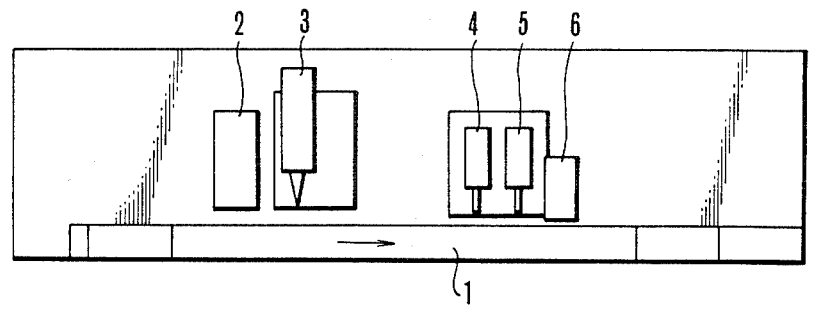
FIG. 1 is an illustration of the configuration of a device for enzymatic immunological estimation in which the nozzle device of the present invention is incorporated.

In FIG. 1, 1 is a transfer route on which a test plate 7 (FIG. 2) carrying an array of reaction cells 8 is transferred in the direction of the arrow. Above the transfer route 1 are placed, in order from upstream to downstream, a seal breaker 2, an injection device 3 for a sample solution, B/F separation device 4, an injection device 5 for a substrate and a photometric device 6.

The devices mentioned above, that is the seal breaker 2, the injection device 3 for a sample solution, the B/F separation device 4, the injection device 5 for a substrate and the photometric device 6, operate as follows: the seal foil of each reaction cell is first broken, after which a predetermined amount of a sample solution is injected in each reaction cell 8 through the upper opening and, when the reaction is completed, the B/F separation is made. A substrate is then injected into the reaction cell which produces an optically detectable change by the activating action of an enzyme labelled on the aforementioned antigen-antibody reaction complex. Finally, the change occurring on the substrate is detected and measured by the photometric device 6.

Figure 2:
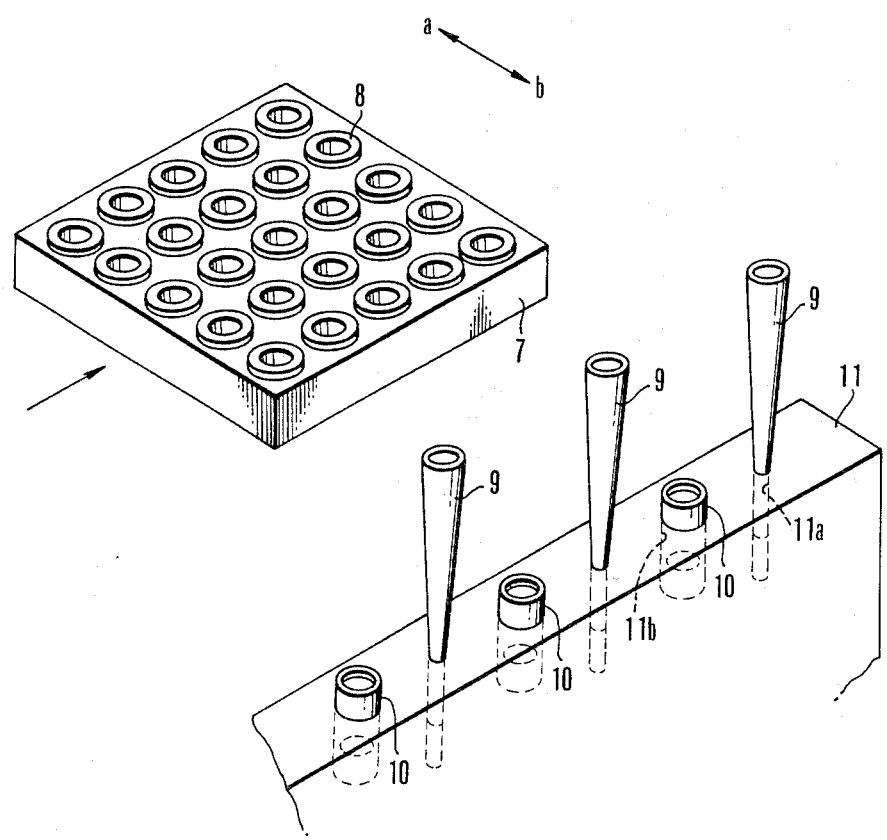
FIG. 2 is an orthogonal view showing the relation between the test plate on which reaction cells are arranged in an array and the pipetting device.

The test plate 7 carries a plurality of the reaction cells 8, with the base of each cell in a cavity (not shown in the Figures) of a cavity array in the test plate 7, as seen in FIG. 2. The plate is moved along the transfer route 1 by a transfer mechanism (not shown in the Figures) in the direction of the arrow in FIG. 1, intermittently and in synchronization with a predetermined timing.

FIG. 2 shows an example of the ready state of the replaceable nozzle tips 9, the ready state being where a nozzle tip corresponds to a sample solution in a cup 10 of the present invention. FIG. 2 also shows the positions of the tips 9 relative to the reaction cells. In FIG. 2 each row of reaction cells extending in the a-b direction and moving in the arrow direction contains the same sample, each cell 8 being used for a different examination. Each nozzle tip 9 and its adjacent cup 10 containing a sample solution (to the left thereof) is used for a single row of reaction cells 8 mentioned above.

The nozzle tip holder 11 may move with the test cups and holds the nozzle tips 9 and the cups 10 containing the sample solutions, as seen in FIG. 2, in fitting holes 11a and 11b, respectively.

Figure 3:
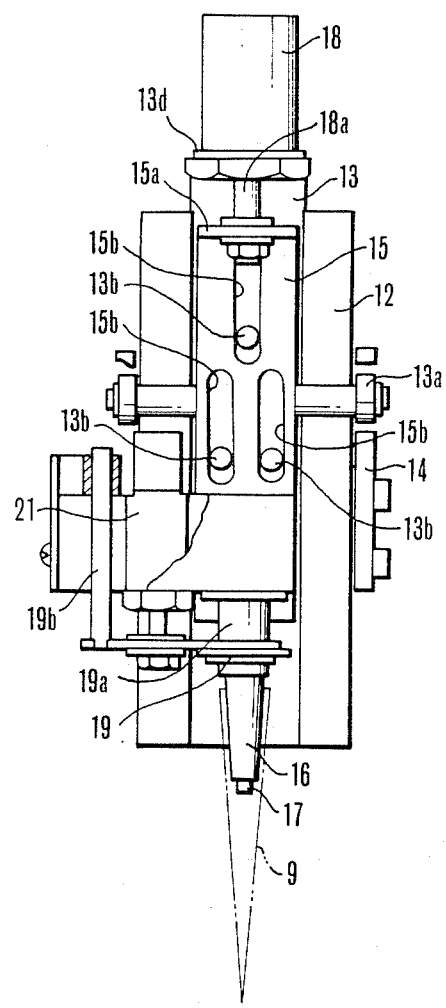
FIG. 3 is a front view of the pipetting device.
Figure 4:
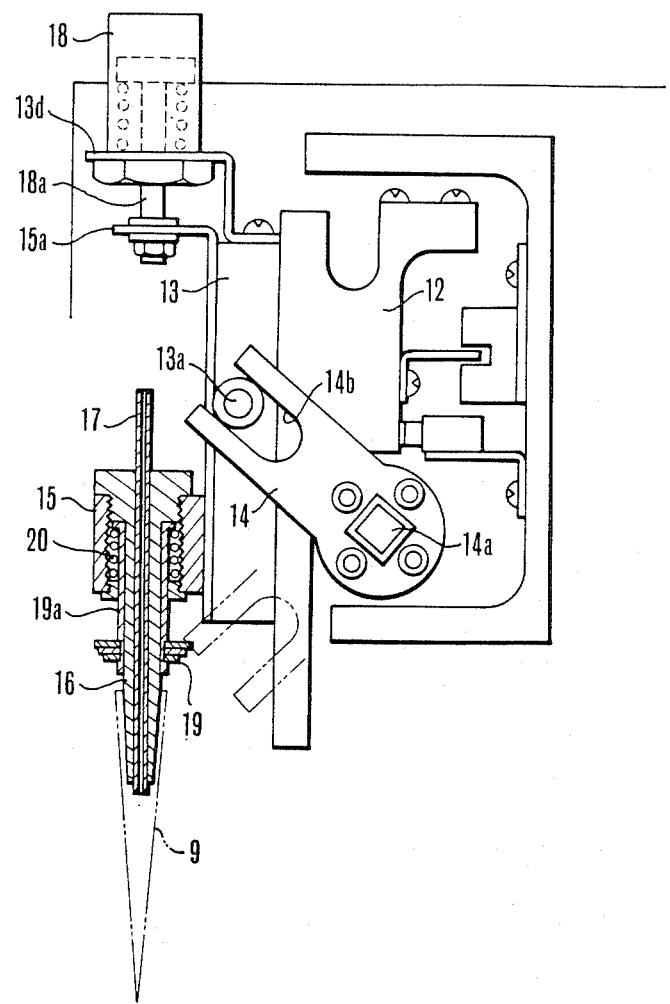
FIG. 4 is a side view of the pipetting device.

FIGS. 3 and 4 show the injection or pipetting device of this embodiment, i.e., element 3 of FIG. 1. At the front of a supporting framework 12 is mounted a slider 13 in a manner so as to be movable in the up and down direction, for example by sliding in a vertical groove of the framework 12. This movement can be effected by the rotation of a fork type cam 14 rotatably mounted on the side wall of the framework 12, within a certain angular range. The rotation of the cam 14 is transmitted to the slider 13 via a pin 13a mounted to the slider 13 and sliding along the fitting recess 14b of the cam 14. The cam is rotated by a driving means such as a pulse motor, not shown in the Figure, which incrementally drives the pivot 14a in rotation. The cam 14 is mounted on the pivot 14a. As the cam rotates between the upper full line position and the lower chain line position, the slider 13 moves along a corresponding vertical length on the framework 12.

A stem supporting bracket 15 supports the stem 16, which is connected thereto by screw threads. The bracket 15 supporting the stem is installed at the front of the slider 13 and is vertically movable relative to the slider 13 by a small stroke while sliding along the front wall of the slider 13. For this purpose, pins 13b protrude from the slider 13 and fit into long vertical holes on the bracket 15 to guide the movement of the latter. Connecting flange 15a at the upper end of the bracket 15 is fixed to a piston rod 18a of a first air cylinder device 18. The first air cylinder device 18 is connected to the slider 13 via flange 13d.

The stem 16, as it is fixed to the bracket 15, permits vertical movement in a two-fold manner; first, a large stroke due to the vertical movement of the slider 13, and second a small stroke due to the vertical movement of the bracket 15 by the air cylinder device 18.

An air pipe 17 is fixed in the stem 16 so as to penetrate the latter in the vertical direction. The upper end of the pipe 17 is connected to an air supply and exhaust device (not shown in the Figure) and the lower end extends to within a nozzle tip 9 which is fittingly applied to the lower end of the stem 16.

According to the above construction, the stem 16 incorporating the air pipe 17 can descend in a large stroke movement, together with the slider 13 to approach a nozzle tip 9 mounted in a holder 11 therebelow, and then in a small stroke movement, due to the air cylinder device 18, until the lower end of the stem is fittingly connected to the nozzle tip without breakage of the tip.

A series of functions which the injection device, constructed as described above, performs during nozzle tip fitting will be discussed below as an example.

A stem 16 which is not yet equipped with a nozzle tip is first placed above and, in facing opposition to, a nozzle tip 9 on a nozzle tip holder 11, either by movement of the holder 11 or by movement of the framework 12. The stem 16 is then lowered by a large stroke due to rotation of cam 14. Then the stem 16 is further lowered by a small stroke via the air cylinder device 18 until the lower end of the stem is fittingly connected with the upper end of the nozzle tip 9. After the fitting of the nozzle tip, the stem 16 is elevated by a small stroke and then by a large stroke to the initial position.

The stem 16 is then positioned with the lower end of the nozzle tip 9 in facing opposition to a cup 10 containing a sample solution. This can be done by movement of either the injection device or the tip holder 11 in the arrow direction of FIG. 2. The stem 16 (hence the nozzle tip 9) is then lowered by a large stroke until the lower end of the nozzle tip 9 dips in the sample solution. Then the solution is sucked from the cup 10. The stem 16 with the nozzle tip 9 at the lower end is then elevated by a large stroke. Finally, the stem 16, together with the nozzle tip 9, is positioned above a desired reaction cell, by movement of either the framework 12 or the test plate 7 in the arrow and/or a-b directions of FIG. 2, lowered by a large stroke and the solution in the nozzle tip 9 is delivered into the reaction cell.

The mechanism to remove the nozzle tip 9 from the stem 16 will now be explained. The mechanism of this example mainly consists of three components. A lever 19 which is placed loosely around the lower end of the stem 16 is used to directly push and remove the nozzle tip 9 from the stem 16. A holding spring 20 arranged outside the sleeve 19a as shown in FIG. 4 serves to hold the lever 19 and its sleeve 19a in the upper position when not in use by bearing against a flange of the sleeve 19a. Another air cylinder device 21 exerts downward force against the lever 19 which in turn presses and removes the nozzle tip 9 from the lower end of the stem 16. A guide bar 19b is provided on which the lever 19 slides when it moves up and down.

The treatment sequence includes operations such as fitting of a nozzle tip to the stem, suction and delivery of a sample solution followed by removal of the nozzle tip from the stem. The operations are repeatedly applied and the timing of each operation may be managed by use of a selected electronic controlling device, generally a microcomputer, which is not shown.

FIG. 5(a) shows an embodiment of the pipetting device in which the supporting framework 12 is supported by a pair of guide rods 31 on the stationary frame 30 so that the framework 12 can be moved in the direction of the axis of the guide rods (the a-b direction). Thus, the supporting framework 12 can be laterally transferred between a nozzle tip fitting position and positions of suction and injection of sample solutions. This movement may be powered by means of a moving device not shown in the Figure.

One end of a rotating rod 33 is connected to a pulse motor 34. The cam 14 is fixed to the rotating rod 33 so that the slider 13 moves in the vertical direction in accordance with the rotation of the rod 33. The bracket 15 supporting the stem 16 fits in a recess which extends vertically on the front surface of the slider 13 so as to move slidingly in the vertical direction, and also the air cylinder device 18 attached to the top of the slider 13 permits a relative up and down movement of the slider by a small stroke. At the lower end of the piston rod extending from the air cylinder device 18, there is fixed the flange 15a of the supporting bracket 15 for connecting the air cylinder.

Further in this example, a lever 37 (FIG. 5(b)) for removing the nozzle tip is installed at the lower part of the supporting bracket 15. The lever 37 can pivot downward about the axis 36 due to the air cylinder device 21 to remove the nozzle tip from the stem 16, but otherwise the lever 37 is held in the horizontal position by a panel spring 35. The stem 16 with a nozzle tip 9 at the lower end extends loosely through a hole 38 in the lever 37, and when the lever 37 is moved by cylinder device 21 and the edge of the hole 38 hits the upper end of the nozzle tip 9, the tip is removed from the stem.

According to the device of the present invention, sample solutions can be injected into a number of reaction cells disposed in an array while the nozzle tips are replaced automatically as necessary. Thus, a plurality of sample solutions can be quantitatively delivered into predetermined reaction cells without any mixing of the solutions with each other, and therefore fear of the significant error that may occur for each sample has been markedly reduced.

When the device of this invention is used, nozzle tips can be replaced for different sample solutions by the automatic pipetting mechanism. Therefore its effect is that a total system of analysis with which an analytical treatment is completely automated can be composed as desired and the usefulness of this invention is remarkable.

Obviously, numerous modifications and variations of the present invention are possible in light of the above teachings. It is therefore to be understood that within the scope of the appended claims, the invention may be practiced otherwise than as specifically described herein.

What is claimed is:

1. A pipetting device comprising:
   a supporting frame;
   a slider mounted on said supporting frame for vertical movement;
   first power driving means for vertically moving said slider by a large stroke;
   a plunger type stem having a lower end fittable within the upper end of an approximately inverted cone shaped nozzle tip, said stem being mounted for vertical movement on said slider;
   means for communicating said lower end of said stem with an air supply and exhaust means, whereby said nozzle tip may be supplied with air or air may be sucked therefrom; and
   second power driving means independent from said first power driving means for vertically moving said stem in two directions on said slider by a small stroke as compared to said large stroke.

2. The device of claim 1 including means for removing a nozzle tip from said stem.

3. The device of claim 2 wherein said removing means comprises a lever mounted loosely on said lower end of said stem, and means for downwardly moving said lever so that said lever applies pressure to a nozzle tip fitted on said stem.

4. The device of claim 2 wherein said first power driving means comprise:
   a fork type cam rotatably mounted on said supporting frame;
   means for rotating said cam about a horizontal axis; and
   pin means mounted on said slider for engagement by said cam, whereby rotation of said cam vertically moves said slider.

5. The device of claim 2 wherein said second power driving means comprises a pneumatic cylinder device mounted to said slider and having a piston fixed relative to said stem.

6. The device of claim 4 wherein said second power driving means comprises a pneumatic cylinder device mounted to said slider and having a piston fixed relative to said stem.

7. The device of claim 2 including means for moving said support frame in a horizontal direction.

8. The device of claim 6 including means for moving said support frame in a horizontal direction.

9. The device of claim 2 in combination with means for supporting a plurality of said nozzle tips in a horizontal array beneath said stem.

* * * * *